(12) United States Patent
Alper et al.

(10) Patent No.: US 8,921,474 B2
(45) Date of Patent: Dec. 30, 2014

(54) HOT MELT ADHESIVE BASED ON OLEFIN BLOCK COPOLYMERS

(75) Inventors: Mark D. Alper, Mukwonago, WI (US); Monina D. Kanderski, Milwaukee, WI (US)

(73) Assignee: Bostik, Inc., Wauwatosa, WI (US)

( * ) Notice: Subject to any disclaimer, the term of this patent is extended or adjusted under 35 U.S.C. 154(b) by 315 days.

(21) Appl. No.: 12/842,807

(22) Filed: Jul. 23, 2010

(65) Prior Publication Data

US 2011/0021103 A1 Jan. 27, 2011

Related U.S. Application Data

(60) Provisional application No. 61/228,435, filed on Jul. 24, 2009.

(51) Int. Cl.
| | |
|---|---|
| *B32B 7/12* | (2006.01) |
| *B32B 5/26* | (2006.01) |
| *B32B 27/12* | (2006.01) |
| *B32B 27/32* | (2006.01) |
| *C09J 153/00* | (2006.01) |
| *C08L 53/02* | (2006.01) |
| *D04H 1/42* | (2012.01) |

(52) U.S. Cl.
CPC .............. *D04H 1/42* (2013.01); *B32B 2309/14* (2013.01); *B32B 2255/02* (2013.01); *B32B 27/12* (2013.01); *B32B 2307/51* (2013.01); *B32B 7/12* (2013.01); *B32B 2255/10* (2013.01); *B32B 2274/00* (2013.01); *B32B 2255/26* (2013.01); *C09J 153/00* (2013.01); *C08L 53/02* (2013.01); *B32B 2272/00* (2013.01); *B32B 27/32* (2013.01); *B32B 5/26* (2013.01); *B32B 2555/02* (2013.01); *B32B 2262/00* (2013.01)
USPC ........... 524/487; 524/505; 442/329; 442/327; 156/325; 525/191

(58) Field of Classification Search
USPC .................. 524/274, 505, 487; 442/329, 327; 156/325; 525/191
See application file for complete search history.

(56) References Cited

U.S. PATENT DOCUMENTS

| | | | |
|---|---|---|---|
| 6,329,468 | B1 | 12/2001 | Wang |
| 6,747,114 | B2 | 6/2004 | Karandinos et al. |
| 7,517,579 | B2 | 4/2009 | Campbell et al. |
| 7,524,911 | B2 | 4/2009 | Karjala et al. |
| 2006/0020067 | A1* | 1/2006 | Brant et al. .................... 524/236 |
| 2008/0081858 | A1* | 4/2008 | Okazaki ........................ 524/274 |
| 2008/0081878 | A1* | 4/2008 | Jiang et al. .................... 525/191 |
| 2008/0306214 | A1 | 12/2008 | Kanderski |

FOREIGN PATENT DOCUMENTS

| | | | |
|---|---|---|---|
| WO | WO 2006/101966 | | 9/2006 |
| WO | WO 2006/102016 | | 9/2006 |
| WO | WO 2008/005501 | | 1/2008 |
| WO | WO 2008/067503 | | 6/2008 |
| WO | WO 2009/029476 | * | 3/2009 |

OTHER PUBLICATIONS

Technical Data Sheet from ExxonMobil for Escorez 2596 Petroleum Hydrocarbon Resin.*
International Search Report/Written Opinion, PCT International Application No. PCT/US2010/043119, mailed Sep. 17, 2010.

* cited by examiner

*Primary Examiner* — James J Seidleck
*Assistant Examiner* — Deve E Valdez
(74) *Attorney, Agent, or Firm* — Wozny Law, LLC; Thomas M. Wozny

(57) ABSTRACT

A hot melt adhesive composition, comprising a blend of components including about 5% to about 50% by weight of an olefin block copolymer; about 10% to about 70% by weight of a first tackifying resin having a softening point of at least about 95° C.; about 0 to 65% of a second tackifying resin that is different than the first tackifying resin; about 0% to about 60% by weight of a plasticizer; about 0% to about 20% by weight of an aromatic reinforcing resin having a softening point equal to or higher than 115° C.; about 0.1% to about 5% by weight of a stabilizer; and about 1% to about 40% by weight of a secondary polymer that is different from the olefin block copolymer, the first and second tackifying resins and the reinforcing resin, having relatively low crystallinity, which low crystallinity is equal to or less than 250 Joules/gram, wherein the components total 100% by weight of the composition, and the viscosity of the composition is equal to or less than about 20,000 mPa·s at 163° C. Laminates, especially those used in disposable soft goods, and methods of making such laminates using the hot melt adhesive composition are also described. The adhesive composition and/or laminate may be used in making a variety of end products such as a disposable diaper, a sanitary napkin, a bed pad, a bandage, a surgical drape, a tape, a label, a plastic sheet, a nonwoven sheet, a paper sheet, a cardboard, a book, a filter, or a package.

24 Claims, No Drawings

HOT MELT ADHESIVE BASED ON OLEFIN BLOCK COPOLYMERS

CROSS REFERENCE TO RELATED APPLICATION

This application claims the benefit of U.S. Provisional Patent Application No. 61/228,435, filed Jul. 24, 2009.

BACKGROUND OF THE INVENTION

The present invention relates to hot melt adhesives, and more particularly to a hot melt adhesive using an olefin block copolymer (OBC) to provide high initial bond resistance for making elastic components such as laminates containing elastic strands for use in disposable diapers.

The increasing complexity of manufactured goods, in particular disposable goods, also leads to major improvements and developments in the hot melt adhesive industry. Hot melt adhesives are being used to bond a wider variety of substrates, within a broader adhesive application process window, and for a large end-use portfolio. For example considering the diaper manufacturing industry, materials involved may be non-woven materials, polymeric films, and in general elastomeric components. These elastomeric components can be used in products like diapers, in a form of strands, films, nonwovens or any other continuous or discrete form.

Processability of hot melt adhesives are linked to their ability to be melted, and transported and/or coated in a molten stage to the final location where the bond is required. Usually the molten adhesive is sprayed, or coated as a film. Once cooled down, the adhesive needs to fulfill multiple requirements, like bond strength measured by peel force or bond retention under or after mechanical stress, and under or after various thermal conditions.

Typically hot melt adhesives can be based on polymers such as polyolefins (ethylene- or propene-based polymers), or functionalized polyolefins (ethylene or propene copolymers with oxygen containing monomers), or styrenic block copolymers containing at least one rubbery phase, like styrene-isoprene-styrene (SIS), or styrene-butadiene-styrene (SBS) polymers. Styrenic block copolymers are of interest due to their dual characteristics, i.e. cohesion of the styrenic phase associated with the rubber behavior of another phase. Typical application temperatures are equal to or higher than 150° C.

Over the years, many different olefinic polymers have been used in the formulation of hot melt adhesives used in the construction of disposable soft goods. The first of these was amorphous polypropylene (APP). This material was produced as a by-product of crystalline polypropylene and was obtained by solvent extraction. This APP polymer could be combined with various tackifiers, plasticizers, waxes, etc. to produce a hot melt that could be used for diaper construction, for example.

Later, polymers became available that were produced on purpose that had much improved properties over the original APP polymers. These were referred to as amorphous poly alpha olefins (APAO). They were primarily produced using Ziegler-Natta catalysis and could be made using a variety of monomers, including but not limited to propylene, ethylene and butene. Various copolymers and terpolymers are produced by a number of manufacturers. They include Evonik Industries, who produce the Vestoplast® polymers; REXtac, LLC, who produces the Rextac® RT range of materials and Eastman Chemical, manufacturers of the Eastoflex® line of polymers. They are all characterized by having a very low degree of crystallinity as measured by DSC. As commercially produced, they are random polymers having broad molecular weight distributions.

When formulated into hot melt adhesives for the construction of disposable articles, they had some deficiencies. They generally lacked elevated temperature heat resistance (particularly creep resistance) so they were not used for elastic attachment. This was due to their amorphous character. While they found widespread use for the diaper construction application (bonding the nonwoven to the polyethylene) they did not possess the level of elevated temperature creep resistance needed for the elastic attachment application.

One other reason APAO based hot melt adhesives were not used for elastic attachment was their poor sprayability. While the construction application is applied in a variety of ways, the elastic adhesive is almost always applied using spray application equipment. Compared to the construction application, the spray application for elastic attachment is must more demanding. The adhesive is generally applied hotter and at a higher add-on level than the construction application. This can lead to burn-through problems if not properly applied. In addition, the elastic application needs to be applied more precisely, that is directly onto the strands of elastic, instead of an overall construction application.

Historically traditional polyolefins such as polyethylene or polypropylene have not been used for any diaper construction applications. While these polymers are used in hot melt adhesives for packaging applications (e.g. case and carton sealing), they lack the adhesion, open time and sprayability needed for disposable applications. Examples of these types of polymers include the Epolene® polymers from Westlake Chemical Company.

More recently, metallocene catalysis has been used to make polyolefins with more precisely tailored properties. For example, the molecular weight of the polymer can be controlled in a way not possible with the older Ziegler-Natta catalysts. Polymers can be made using high levels of comonomer, such as butene-1 and octene-1, to produce polymers with very low levels of crystallinity and density. While these polymers have been used to make hot melt adhesives with better adhesion characteristics, they have not been widely used in the Nonwovens industry because of their lack of sprayability. Examples of these metallocene polymers include Affinity® and Engage® polymers from Dow Chemical Company.

The standard in the disposable industry in terms of sprayability have been hot melts based on styrenic block copolymers, specifically styrene-isoprene-styrene (SIS) block copolymers. No olefinic based polymer has been able to match the characteristics of the styrenic block copolymers in terms of ease of sprayability and application window. The term "application window" means the range of conditions a given adhesive will apply well. For example, if a given hot melt adhesive can only be applied over a narrow range of temperatures, flow rates, air pressures, open times, etc. it is described as having a narrow application window. If on the other hand an adhesive can be applied over a wide range of conditions and still give acceptable bonds, it is described as having a broad application window. It is very important that products used in the manufacture of disposable goods have a broad application window to minimize downtime and scrap during line speed fluctuations that occur during line start-up for example, or temperature fluctuations that might happen during production. Since these manufacturing lines frequently operate at line speeds over 1000 feet per minute, it is important to minimize scrap.

Polyolefin polymers are produced in a very wide range of molecular weights, monomers, densities and crystallinity levels. They are also made using an ever widening range of catalysts. There are Ziegler-Natta catalysis, metallocene and other single cite catalysts and more recently those that can produce block polyolefins.

These polymers range in crystallinity from very low, such as with amorphous polypropylene or amorphous poly-alpha-olefins to those that are very high, such as isotactic polypropylene. The crystallinity of a polymer can be determined by Differential Scanning Calorimetry (DSC) or X-ray Diffraction techniques. DSC is the most widely used technique by far. The Enthalpy of Fusion (also known as latent heat of melting or heat of fusion) can be measured and quantified using ASTM E793-01 entitled "Standard Test Method of Enthalpies of Fusion and Crystallization by Differential Scanning Calorimetry". The enthalpy of fusion is the amount of energy it takes to melt the crystalline portion of the polymer. This value is generally reported in Joules/gram (J/g).

This number varies widely from almost zero to upwards of 250 Joules/gram depending on the crystallinity of the polymer. Ideally, a truly amorphous polymer would have no crystallinity, no melting point and therefore an enthalpy of fusion of zero. As it states in U.S. Pat. No. 7,524,911 (column 8, lines 30-33), "The term 'amorphous' refers to a polymer lacking a crystalline melting point as determined by differential scanning calorimetry (DSC) or equivalent technique".

As a practical matter, most polymers that are sold as "amorphous poly-alpha-olefins" (APAO) have some low level of crystallinity. On the other hand, polymers that are considered crystalline are not 100 percent crystalline. In the '911 patent it states at column 8, lines 26-30, "The term 'crystalline' refers to a polymer that possesses a first order transition or crystalline melting point (Tm) as determined by differential scanning calorimetry (DSC) or equivalent technique, and this term may be used interchangeably with the term 'semicrystalline'."

It is useful to have some quantifiable boundary between what is considered "amorphous" polymer and those considered "semi-crystalline" or "crystalline". In U.S. Pat. No. 6,747,114 it states at column 8, lines 9-14, "The semi-crystalline polymer preferably has a heat of fusion from about 30 J/g to about 80 J/g as determined by DSC, more preferably from about 40 J/g to about 70 J/g as determined by DSC, and most preferable from about 50 J/g to about 65 J/g as determined by DSC."

Bostik's internal analysis correlates with the descriptions above. The "amorphous poly-alpha olefins" are not in fact entirely amorphous and possess a very low level of crystallinity as measured by DSC. The analysis of many of the grades sold by Eastman Chemical Co. as "Amorphous Polyolefins" under the trade name Eastoflex® and those sold by Evonik Industries as "Amorphous Poly-alpha-olefins" under the trade name Vestoplast® and those manufactured by REXtac, LLC. as REXtac RT show that all of them have an enthalpy (or heat) of fusion of less than 25 Joules/gram. The single highest value obtained was 20.4 Joules/gram for Vestoplast® 708. One of the two grades shown in U.S. Pat. No. 7,517,579 (assigned to Kimberly-Clark Worldwide, Inc.) is RT2730, which has a heat of fusion of 9.4 Joules/gram. The other grade that is mentioned is RT2723, which according to REXtac's usual nomenclature should be a lower viscosity version of RT2730 with the same monomer ratios. Therefore, the enthalpy of fusion should be similar to RT2730. In summary, currently available data strongly indicates that any grade of polymer currently sold as an "amorphous poly-alpha-olefin" would have an enthalpy of fusion value of less than about 25 Joules/gram.

A wide range of other polyolefins are produced by a variety of manufacturers that fall under the category of "semi-crystalline" polymers. They have heat of fusion values of greater than about 30 Joules/gram, which puts them outside the range of APAO's. For example, ethylene vinyl acetate copolymers range from about 35 Joules/gram for a high vinyl acetate grade (40% VA) to about 73 Joules/gram for a lower vinyl acetate grade (18% VA). Polyalphaolefins such as Dow's Affinity® grades (ethylene/octane copolymers) range from about 52 Joules/gram for Affinity® 8200, a relatively low density grade (0.870 g/cc, MI=5) to 77 J/g for a higher density grade (0.900 g/cc, MI=6) called Affinity® PL 1280. Dow also manufacturers a high melt index grade (0.870 g/cc, MI=1000) called GA1900 specifically for hot melt adhesives that has a heat of fusion of 57 Joules/gram. Clearly, these Affinity® polymers could not be considered to be amorphous and are not amorphous poly-alpha-olefins.

A more recent development in the area of polyolefins is what are referred to as "olefin block copolymers" or OBC. This is an entirely new class of polyolefin polymer produced using a chain shuttling catalysis technology that produces a linear block structure of the monomers rather than a random polymer produced by Ziegler-Natta or traditional metallocene technology. At this time, they are manufactured by Dow Chemical under the trade name of Infuse®. The OBC's consist of crystallizable ethylene-octene blocks (hard) with very low comonomer content and high melting temperature alternating with amorphous ethylene-octene blocks (soft) with high comonomer content and low glass transition temperature. This gives the polymer much better elevated temperature resistance and elasticity compared to a typical metallocene random polymer of similar density. While some of the grades of Infuse® have low heat of fusion (approximately 20 Joules/gram) they could not be considered to be amorphous poly-alpha-olefins because the polymer architecture is completely different (i.e. block vs. random) and is specifically produced to have crystalline regions. Not only are they different on a structural basis, they are very different from a physical property standpoint with the OBC's having better elastic recovery, compression set and elevated temperature resistance. As such, they are sold into different markets for different end uses and are not considered equivalent for one another.

U.S. Pat. No. 7,524,911 and WO 2009/029476 disclose adhesive compositions based on olefin block copolymers (OBC). Other references disclosing OBC's and various applications for OBC's include WO 2006/101966, WO 2006/102016, WO 2008/005501, and WO 2008/067503.

SUMMARY OF THE INVENTION

The present invention is based on a unique formulation using an olefin block copolymer (OBC), particularly for elastic attachment and construction in diaper structures. The present invention solves the very important requirement of having a sprayable, olefinic-based hot melt adhesive using the same application techniques as currently used, like coating techniques and add-on levels, and providing the end-use application the same level of performance expected with the current SIS and SBS based technologies, i.e. high bond strength levels in term of creep resistance, peel force and in general bond retention with mechanical resistance and heat resistance. When formulated into a hot melt adhesive, OBC's offer improved spray characteristics compared to APAO based adhesives or those based on the older generations of polyolefins. In particular, when formulated in combination with an APAO or other polymers with low crystallinity, a hot melt adhesive can be produced with a unique combination of adhesion, elevated temperature creep resistance and sprayability. This combination of properties has not previously been achieved without using a styrenic block copolymer. In addition, compared to conventional SIS based or SBS based adhesives, OBC offers improved viscosity stability when stored at elevated temperatures. Finally, OBC is thermally stable at elevated temperatures.

Various methods are conventionally used to coat a hot melt adhesive at fairly low viscosity on a substrate. This can be made by roll coating or any printing type method, or by slot coating, by extrusion or by spray gun. Spray gun techniques are numerous and can be done with or without assistance of compressed air that would shape the adhesive spray, and consequently the adhesive pattern. The hot melt adhesive material is generally allowed to melt in tanks, and then pumped through hoses to the final coating spot on the substrates. For the present invention, preferred methods of applying the adhesive would be by spray application, most preferably assisted by air. Among these techniques, the most common are spiral spray (Controlled Fiberization™ by Nordson), Summit™ by Nordson, Surewrap™ by Nordson, Omega™ by ITW, Curtain Coating™ by Nordson and various melt blown processes.

For the present invention, the temperature at which the hot melt adhesive is applied should be below 170° C., so that heat sensitive substrates would not be damaged. Preferably, this temperature should be equal to or lower than 150° C.

Also, the viscosity (as measured via ASTM D3236-88) of the adhesive material should be generally lower than 20,000 mPa·s, more preferably lower than 15,000 mPa·s, most preferably lower than 12,000 mPa·s measured at 163° C. (325° F.). An adhesive with such low viscosity is needed to be operated through standard hot melt adhesive equipment and to achieve the right pattern and consequently the right bonding performance at the application temperature.

The adhesive of the present invention can be used with any process of conventional construction or elastic attachment technology as known in the state of the art.

The adhesive of the present invention can be used with any application where various substrate materials are involved like non-woven materials, polymeric films, and in general elastomeric components put in items like diapers, in the form of strands, films, nonwovens or any other continuous or discrete form. Any substrate material and any substrate form could be used in any combination possible, the adhesive allowing to bond two or more substrates together. The substrates can be of multiple forms for example fiber, film, thread, strip, ribbon, coating, foil, sheet, and band. The substrate can be of any known composition for example polyolefin, polyacrylic, polyester, polyvinyl chloride, polystyrene, cellulosic like wood, cardboard and paper, or made out of mineral compounds like concrete, glass or ceramics. The substrate's mechanical behavior can be rigid, plastic or elastomeric. Among elastomeric material are various examples like natural or synthetic rubber, polyurethane based copolymers, polyether or polyester urethanes, block copolymers of styrene or of amides, or olefinic copolymers. The above lists are not limitative or all-inclusive, but are only provided as common examples. In the present invention, various methods to process hot melt adhesives can be employed, linked to their ability to be melted, and transported and/or coated or sprayed in a molten stage to the final location where the bond is required.

The adhesive of the present invention can also be used with any application where composites and disposable products are made with the help of bonding parts together with a hot melt adhesive used at a temperature lower than 170° C., preferably equal to or lower than 150° C., while obtaining adequate cohesion from the adhesive bond to withstand mechanical stress at low, ambient or elevated temperature, in particular under creep conditions. Diaper, adult incontinence products, sanitary napkins and other absorbent disposable products are envisioned applications for the adhesive composition of the invention, as well as bed pads, absorbing pads, surgical drapes and other related medical or surgical devices. Construction applications, structural applications or packaging applications, in particular disposable items packaging and food packaging, can also be applications where the invention is useful. The most specific application of the present hot melt adhesive is for elastic attachment, wherein the present invention allows bonding of elastic strands on film substrates while applying the adhesive at a temperature lower than 170° C., preferably equal to or lower than 150° C.

Good performance for elastic attachment in a diaper application is typically when the bond retention is either more than 60%, preferably more than 70%, more preferably more than 75%, most preferably more than 80% in a specific test described hereinafter when it is done within 2 days after adhesive has been applied on substrates (initial creep test). These tests are indicative of what level of adhesion and creep resistance (or bond retention) can be achieved by an adhesive. Because of economics involved in production and in material cost, preferred adhesive add-ons for a spiral spray application are lower than 18 gsm ("gsm" refers to grams of adhesive material per square meter of substrate covered by the adhesive material), more preferably equal to or lower than 15 gsm, and most preferably equal to or lower than 12 gsm. If individual strand coating techniques are used, the add-on level is generally less than 60 mg/strand/meter. For construction applications, the add-on level is typically 6 grams/square meter or less. For other applications, the add-on levels will vary depending on the specific end use requirements.

Accordingly, the present invention provides a hot melt adhesive composition, comprising a blend of the following components:

about 5% to about 50%, preferably about 10% to about 30%, and most preferably about 12% to about 20%, by weight, of an olefin block copolymer (OBC);

about 10% to about 70%, preferably about 40% to about 65%, and most preferably about 50% to about 60%, by weight, of a first tackifying resin having a softening point of at least about 95° C. and preferably a softening point of from about 95° C. to about 140° C.;

about 0% to about 65% of a second tackifying resin that is different than the first tackifying resin;

about 0% to about 60%, preferably about 2% to about 30%, more preferably about 3% to about 20%, by weight, of a plasticizer;

about 0% to about 20%, preferably about 2% to about 15%, more preferable about 4% to about 12%, and most preferably about 6% to about 10%, by weight of an aromatic reinforcing resin having a softening point equal to or greater than 115° C.;

about 0.1% to about 5% of a stabilizer or antioxidant; and about 1% to about 40%, preferably about 2% to about 35%, and more preferably about 2% to about 30%, by weight of a secondary polymer different from the OBC, the first and second tackifying resins and the reinforcing resin, having relatively low crystallinity, which low crystallinity is equal to or less than 250 Joules/gram (J/g), preferably equal to or less than 150 Joules/gram, and more preferably equal to or less than 100 Joules/gram; as well as blends of each of the above components;

wherein the components total 100% by weight of the composition, and the viscosity (measured by ASTM D3236-88) of the composition is equal to or less than about 20,000 mPa·s at 163° C. (325° F.), preferably equal to or less than 15,000 mPa·s at 163° C., and more preferably equal to or less than 12,000 mPa·s at 163° C.

Although the primary polymer component in the present adhesive composition is an OBC, and the secondary polymer should have relatively low crystallinity, blends of the OBC and secondary polymer containing about 1% to about 25% by weight, preferably about 1% to about 15% by weight of an additional auxiliary polymer comprising EVA or a styrenic block copolymer such as, SIS, SI, SBS, SB, SIBS, SEB, SEBS, SEP, SEPS, SBBS, SEEPS and blends of each thereof, may also be used as long as the additional auxiliary polymer is compatible. The auxiliary polymer is a polymer that is different from the OBC, the first and second tackifying resins, the reinforcing resin, and the secondary polymer, and functions to provide a desired physical property, depending on the end use of the adhesive composition.

Relatively small amounts (0-20% by weight) of a more crystalline material such as a wax may also be used as long as it does not interfere with the level of performance required by the end use.

The present invention also provides a laminate comprising a first layer of nonwoven material, a second layer of nonwoven material, and one or a plurality of elastomeric substrates, disposed between said first and second nonwoven layers, bonded together with the OBC-based adhesive composition.

The laminate may also comprise a first layer of nonwoven material, a second layer of film material, and one or a plurality of elastomeric substrates disposed between said first and second layers, bonded together with the OBC-based adhesive composition. The film material may comprise a polyethylene film, a polypropylene film, an ethylene-propylene copolymer film or a cloth-like coated film material, and the elastomeric substrate is preferably a plurality of elastic strands.

The laminate may further comprise a first layer of nonwoven material bonded to a second layer of film or nonwoven material with the adhesive composition, and without any elastomeric substrate therebetween.

The adhesive composition and/or laminate of the present invention may be used in making a variety of end products. Examples include a disposable diaper, a sanitary napkin, a bed pad, a bandage, a surgical drape, a tape, a label, a plastic sheet, a nonwoven sheet, a paper sheet, a cardboard, a book, a filter, or a package.

In yet another aspect, the present invention provides a method of making a laminate comprising the steps of feeding a first substrate in a first direction; feeding a second substrate spaced from said first substrate in said first direction; applying the adhesive composition to one or both of said substrates; and compressing said substrates together to form the laminate.

When an elastomeric laminate is desired, the method includes the additional steps of feeding one or a plurality of elastomeric substrate or substrates between said first and second substrates in said first direction, said elastomeric substrates are stretched before, during or after adhesive application; and applying the adhesive composition to either said elastomeric substrate or substrates or one or both of said substrates before compressing the substrates together. The elastomeric substrate is preferably a plurality of elastic strands each stretched up to 500% from their initial relaxed state.

DETAILED DESCRIPTION OF THE INVENTION

A tackifying resin, as defined in the present description can be a molecule or a macro-molecule, generally a chemical compound or a fairly low molecular weight polymer, compared to common polymers, from a natural source or from a chemical process or combination thereof that in general enhances the adhesion of a final hot melt adhesive composition.

The hot melt adhesive compositions of the present invention also comprises a solid tackifier which is compatible with the OBC copolymer. Representative resins include the $C_5/C_9$ hydrocarbon resins, synthetic polyterpenes, rosin, rosin esters, natural terpenes, and the like. More particularly, the useful tackifying resins include any compatible resins or mixtures thereof such as (1) natural and modified rosins including gum rosin, wood rosin, tall oil rosin, distilled rosin, hydrogenated rosin, dimerized rosin, and polymerized rosin; (2) glycerol and pentaerythritol esters of natural and modified rosins, including the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natural terpenes, such as styrene/terpene and alpha methyl styrene/terpene; (4) polyterpene resins generally resulting from the polymerization of terepene hydrocarbons, such as the bicyclic monoterpene known as pinene, in the presence of Friedel-Crafts catalysts at moderately low temperatures; also included are the hydrogenated polyterpene resins; (5) phenolic modified terpene resins and hydrogenated derivatives thereof such, for example, as the resin product resulting from the condensation, in an acidic medium, of a bicyclic terpene and a phenol; (6) aliphatic petroleum hydrocarbon resins resulting from the polymerization of monomers consisting primarily of olefins and diolefins; also included are the hydrogenated aliphatic petroleum hydrocarbon resins; and (7) cyclic petroleum hydrocarbon resins and the hydrogenated derivatives thereof. Mixtures of two or more of the above described tackifying resins may be required for some formulations. Also included are the cyclic or acyclic $C_5$ resins and aromatic modified acyclic or cyclic resins.

The tackifying resin should have a Ring and Ball softening point (measured by ASTM E28) of at least about 95° C., and preferably between about 95° C. and about 140° C., and most preferably the softening point is between about 95° C. and about 115° C. A preferred tackifier is a hydrogenated aromatic modified dicyclopentadiene resin with a Ring and Ball softening point between about 100° C. to 115° C. The most preferred tackifying resins are fully hydrogenated resins regardless of type like aliphatic or cycloaliphatic hydrocarbon resins such as, Eastotac® H100W, or Sukorez® SU210, a pure aromatic monomer resin such as Regalrez 1094, and DCPD (dicyclopentadiene) resins with no aromatic content such as Escorez 5400.

Also, other preferred tackifying resins are partially hydrogenated aliphatic hydrocarbon resins such as Eastotac H100L and Eastotac H100R, as well as non-hydrogenated aliphatic C5 resins and aromatic modified C5 resins with low aromaticity such as Piccotac 1095 and Piccotac 9095, respectively.

The tackifiers are generally present in the adhesive compositions in an amount greater than the amount of the OBC block copolymer. Within this range, amounts of about 10 to 70% by weight of the composition, preferably about 40 to 65% by weight are utilized, and most preferably about 50 to 60% by weight. Blends of two or more tackifying resins may also be used. For example, a blend of a first tackifying resin and a second tackifying resin that is different than the first tackifying resin may also be employed. From about 0% to about 65% by weight of one or more additional tackifying resins may be blended together with the first tackifying resin if desired.

The primary polymer component used in a hot melt adhesive formula according to the present invention is an olefin block copolymer (OBC).

An "olefin block copolymer" or OBC is a more recent development in the area of polyolefins. This is an entirely new class of polyolefin polymers produced using a chain shuttling catalysis technology that produces a linear block structure of the monomers rather than a random polymer produced by Ziegler-Natta or traditional metallocene technology. At this time, they are manufactured by Dow Chemical under the trade name of Infuse®. The OBC's consist of crystallizable ethylene-octene blocks (hard) with very low comonomer content and high melting point alternating with amorphous ethylene-octene blocks (soft) with high comonomer content and low glass transition temperature. This gives the polymer much better elevated temperature resistance and elasticity compared to a typical metallocene random polymer of similar density. These polymers are described in WO 2006/101966 and others assigned to Dow Chemical Co.

Olefin block copolymers should not be considered amorphous poly-alpha-olefins because the polymer architecture is completely different (i.e. block vs. random) and is specifically produced to have crystalline regions. In addition, OBCs are significantly narrower in poly-dispersity than other traditionally used olefins, for example APAOs, which impacts their melt profiles as measured by DSC (Differential Scanning Calorimetry). It is these structural differences, in combination with the narrow poly-dispersity of OBCs that provides a hot melt adhesive with improved hot tack, adhesion, and cold temperature flexibility without affecting its overall high temperature resistance.

The OBC copolymer may be incorporated into the composition in amounts of from about 5% to about 50% by weight, preferably from about 10% to about 30% by weight, and most preferably from about 12% to about 20% by weight. Olefin block copolymers (OBCs) are polyolefins with alternating blocks of hard (highly rigid) and soft (highly elastomeric) segments. The block structure of OBCs offers an advantaged performance balance of flexibility and sprayability compared to random polyolefin copolymers. OBC is commercially available from Dow Chemical Company under the tradename "Infuse®" in different grades which are distinguishable primarily based on their density and weight % crystallinity as follows:

| OBC Grade | Density (g/cm$^3$) | Melt Index (MI) |
|---|---|---|
| Infuse 9817 | 0.877 | 15 |
| Infuse 9807 | 0.866 | 15 |

OBCs are well known in the art. Details of their synthesis and physical properties can be found in, for example, WO 2006/101966, WO 2006/102016, WO 2006/102150, WO 2009/029476 and U.S. Pat. No. 7,524,911, the disclosures of which are specifically incorporated herein by reference. As is known in the art, the density of the OBC is directly related to its crystallinity, i.e. the higher the density the higher the percent crystallinity. OBC's useful in the present hot melt adhesive composition have densities ranging from 0.860 g/cm$^3$ to 0.900 g/cm$^3$ and a melt index of 1 g/10 min. to 1000 g/10 min, preferably 1 g/10 min to 100 g/10 min. as measured according to ASTM D1238 at 190° C. with a 2.16 kg weight.

Blends of two or more OBC polymers may also be used. For example, a blend of a first OBC polymer and a second OBC polymer that is different than the first OBC polymer may be employed.

In addition to OBC, the hot melt adhesive composition also comprises about 1% to about 40%, preferably about 2% to about 35% and most preferably about 2% to about 30% by weight of a secondary polymer having relatively low crystallinity, which low crystallinity is equal to or less than 250 Joules/gram, preferably equal to or less than 150 Joules/gram, and more preferably equal to or less than 100 Joules/gram (J/g). In some embodiments, the crystallinity is equal to or less than about 80 J/g, and in other embodiments equal to or less than about 50 J/g, and in still other embodiments equal to or less than about 25 J/g. Thus, the secondary polymer encompasses both amorphous poly-alpha-olefins (APAO's) and crystalline or semi-crystalline polymers previously discussed herein. The secondary polymer is a polymer that is different from the OBC, the first and second tackifying resins, and the reinforcing resin. For example, the secondary polymer can function to maintain a relatively low viscosity for the composition without significantly affecting bond strength to substrates such as polyethylene.

As used herein, the term "secondary polymer" refers to thermoplastic materials composed of a homopolymer, a copolymer, a terpolymer and/or blends of homopolymers, copolymers, or terpolymers. Either a single secondary polymer may be used, or mixtures of two or more secondary polymers may be incorporated into the adhesive composition, depending upon the formulation desired, as long as crystallinity is below 250 J/g.

Any of a variety of well-known and readily available thermoplastic materials can also be used as the secondary polymer in the adhesive compositions. Examples of such materials include ethylene based polymers, including ethylene vinyl acetate, ethylene acrylate, ethylene methacrylate, ethylene methyl acrylate, ethylene methyl methacrylate, ethylene-styrene interpolymer (ESI), ethylene acrylic acid, ethylene vinyl acetate carbon monoxide, and ethylene N-butyl acrylate carbon monoxide; polybutene-1 polymers or copolymers; polyolefins such as high and low density polyethylene; polyethylene blends and chemically modified polyethylene, copolymers of ethylene and $C_1$-$C_8$ mono- or di-unsaturated monomers; polyamides; polybutadiene rubber; polyesters such as polyethylene terephthalate, and polybutylene terephthalate; thermoplastic polycarbonates; amorphous polyalphaolefins (APAO); atactic polyalphaolefins, including atactic polypropylene, polyvinylmethylether and others; thermoplastic polyacrylamides, such as polyacrylonitrile, and copolymers of acrylonitrile and other monomers such as butadiene styrene; polymethyl pentene; polyphenylene sulfide; aromatic polyurethanes; polyvinyl alcohols and copolymers thereof; polyvinyl acetate and random copolymers thereof; styrene-acrylonitrile, acrylonitrile-butadiene-styrene, styrene-butadiene rubbers, acrylonitrile-butadiene-styrene elastomers, A-B, A-B-A, A-(B-A)$_n$-B, (A-B)$_n$-Y block copolymers wherein the A block comprises a polyvinyl aromatic block such as polystyrene, the B block comprises a rubbery midblock which can be polyisoprene or polybutadiene, and optionally hydrogenated, Y comprises a multivalent compound, and n is an integer of at least 3, and mixtures of said substances. Examples of these latter block copolymers including styrene-butadiene, styrene-butadiene-styrene, styrene-isoprene-styrene, styrene-ethylene-butylene-styrene, styrene-ethylene propylene-styrene and styrene-ethylene-ethylene-proplyene-styrene.

Block copolymers are available from Kraton Polymers, Enichem, Fina and Dexco. Multiblock or tapered block copolymers (the A-(B-A)$_n$-B type) are available from Firestone.

Other secondary polymers that could be used are syndiotactic polypropylene (SPP) polymers and/or blends of SPP with amorphous atactic poly-α-olefins (APAO), all of which are well known in this art. The SPP polymers are essentially high molecular weight stereospecific propylene homopolymers or copolymers of propylene with other α-olefin monomers such as ethylene, butene-1 or hexene-1. APAO polymers are a family of essentially amorphous low molecular weight homopolymers or copolymers of propylene or ethylene with an alpha-olefin comonomer.

The thermoplastic polymer material comprising the secondary polymer may be composed of a thermoplastic material or blends of thermoplastic materials which are preferably selected from the group consisting of polyolefins, acrylic modified polyolefins, vinyl acetate modified polyolefins, and acrylic polymers. The polyolefin may be polypropylene or polyethylene. The acrylic modified polyolefin may be a copolymer of polypropylene or polyethylene and an acrylic. Likewise, the vinyl acetate modified polyolefin may be a copolymer of polypropylene or polyethylene and vinyl acetate.

The thermoplastic polymer material comprising the secondary polymer is preferably a suitable single site or metallocene catalyzed ethylene-based copolymer comprising a major portion by weight of ethylene and a minor portion by weight of a $C_3$ to $C_{18}$ alpha-olefin comonomer, or a single site or metallocene catalyzed propylene-based copolymer comprising a major portion by weight of propylene and a minor portion by weight of a $C_2$ to $C_{18}$ alpha-olefin comonomer, or a blend of the ethylene-based copolymers, the propylene-based copolymers, or one or more of the ethylene-based copolymers with one or more of the propylene-based copolymers. The alpha-olefin comonomer preferably contains 3 to 12 carbon atoms, more preferably contains 4 to 10 carbon atoms, and most preferably contains 4 to 8 carbon atoms. More particularly, the alpha-olefin comonomer may be selected from 1-butene, 1-pentene, 3-methyl-1-butene, 3-methyl-1-pentene, 1-hexene, 4-methyl-1-pentene, 1-dodecene, 3-methyl-1-hexene, 1-octene, and 1-decene. Particularly preferred is 1-butene or 1-octene copolymerized with ethylene.

The alpha-olefin comonomer content in the ethylene-based copolymer is at least 20% by weight and in the range of from 20% to 50% by weight, preferably from 25% to 50% by weight, more preferably from 30% to 50% by weight. Suitable ethylene-based copolymers have a density as determined by ASTM D-792 of 0.90 g/cm$^3$ or less and in the range of from 0.90 g/cm$^3$ to 0.85 g/cm$^3$, preferably between 0.89 g/cm$^3$ and 0.85 g/cm$^3$, and most preferably between 0.885 g/cm$^3$ and 0.85 g/cm$^3$. Suitable ethylene-based copolymers also have a melt index at 190° C. and 2.16 kg as determined by ASTM D1238 of greater than 10 g/10 min., preferably greater than 50 g/10 min., and more preferably greater than 100 g/10 min.

The alpha-olefin comonomer content in the propylene-based copolymer is at least 5%, preferably 5% to 30%, and most preferably 5% to 15% by weight, and the preferred copolymer is a propylene-ethylene copolymer. The propylene-based copolymers have a melt index (measured at 230° C.) of more than 10 g/10 min., preferably more than 50 g/10 min. and more preferably more than 100 g/10 min.

"Blends" may comprise two or more ethylene-based copolymers or two or more propylene-based copolymers, or one or more ethylene-based copolymers with one or more propylene-based copolymers. Where a blend of copolymers is used, the calculated density of the blend should also fall within the above limits, i.e. less than 0.900 g/cm$^3$, but greater than 0.850 g/cm$^3$. For example, a blend of 70% of an ethylene-based copolymer having a density of 0.870 g/cm$^3$ and 30% of a propylene-based copolymer having a density of 0.885 g/cm$^3$ will result in a final blend having a calculated density of 0.875 g/cm$^3$.

Useful single site or metallocene catalyzed ethylene-based polymers are available from, among others, Dow Chemical Company and Exxon Mobil Chemical Company who are producers of single site or constrained geometry catalyzed polyethylenes. These resins are commercially available as the AFFINITY™ and EXACT™ polyethylenes.

The single site or metallocene catalyzed propylene-based copolymers are available under the VERSIFY™ brand from The Dow Chemical Company. The manufacture of such polypropylenes is also based on using a metallocene or single site catalyst system and is based on Dow's INSITE™ technology.

The secondary polymer functions to modify specific polymer functions to modify specific physical properties and/or characteristics of the OBC based adhesive composition, as desired. For example, the addition of one or more secondary polymers could be used to increase or decrease (i) the elasticity of the adhesive composition; (ii) the adhesion of the adhesive composition; (iii) the low temperature resistance of the adhesive composition; (iv) the high temperature resistance of the adhesive composition; (v) the creep resistance of the adhesive composition; (vi) the cohesive strength of the adhesive composition; (vii) the pressure sensitivity characteristics of the adhesive composition, (viii) the viscosity characteristics of the adhesive composition and/or (ix) the aging characteristics of the adhesive composition. The relative change (increase or decrease) of the above characteristics is measured relative to the adhesive composition without the addition of the secondary polymer. Thus, for example, Kraton G1652 or Kraton G1657, both of which are styrene/ethylene-butylene/styrene (SEBS) block copolymers, may be added to provide increased elongation characteristics to the OBC polymer in order to increase the elasticity of the adhesive composition. Increased elasticity results in better sprayability characteristics for the adhesive composition. In another example, Eastoflex 1003 or Eastoflex 1060, both ethylene based APAO's, may be added to provide increased adhesion characteristics for the composition, if desired.

The present invention may also include about 0% to about 20%, preferably about 2% to about 15%, more preferably about 4% to about 12%, and most preferably about 6% to about 10%, by weight of an aromatic reinforcing resin having a softening point equal to or greater than 115° C. Examples of such reinforcing resins can be prepared from any substantially aromatic monomers having a polymerizable unsaturated group. Typical examples of such aromatic monomers include the styrenic monomers, styrene, alphamethyl styrene, vinyl toluene, methoxy styrene, tertiary butyl styrene, chlorostyrene, coumarone, indene monomers including indene, and methyl indene. The Ring and Ball Softening Points of the aromatic reinforcing resin is preferably between 115° C. and 160° C. More preferably, the softening point is between about 115° C. and 140° C. and most preferably between about 120° C. and 140° C. Preferred examples are Plastolyn 240, Plastolyn 290 and Plastolyn R1140 available from Eastman Chemical. They have Ring and Ball Softening Points of 120° C. or 140° C.

As used herein, the term "elasticity" is the ability of a material to recover its original shape partially or completely after the deforming force has been removed.

As used herein, the term "adhesion" means the state in which two surfaces are held together by interfacial forces, which may be a combination of valence forces or interlocking action, or both.

As used herein, the term "low temperature resistance" means the relative ability of an adhesive to retain its bond strength and structural integrity at relatively low temperatures (i.e. below room temperature).

As used herein, the term "high temperature resistance" means the relative ability of an adhesive to retain its bond strength and structural integrity at elevated temperatures (e.g. body temperature or warehouse conditions).

As used herein, the term "creep resistance" means the ability of an adhesive to maintain stretched elastic strands in place without significant slippage.

As used herein, the term "cohesive strength" means the degree of internal strength of a material to resist deformation. Various ways of determining cohesive strength exist, such as a tensile test method using a Instron type tensile tester.

As used herein, the term "pressure sensitivity" means the ability of an adhesive to form a bond to a substrate using only pressure.

Although OBC is the primary polymer component, the adhesive composition may also optionally contain blends of OBC with about 1% to about 15% by weight of another auxiliary polymer. Examples of these latter auxiliary polymers that may be used with OBC in hot melt adhesive compositions include, but are not limited to styrenic block copolymers (SBC) and include styrene-butadiene (SB), styrene-isoprene (SI), styrene-isoprene-butadiene-styrene (SIBS), styrene-ethylene-butylene-styrene (SEBS), styrene-ethylene-butylene (SEB), styrene-ethylene propylene-styrene (SEPS), styrene-isoprene-styrene (SIS), styrene-butadiene-styrene (SBS), styrene-butadiene-butadiene-styrene (SBBS), ethylene-vinyl-acetate (EVA), styrene-ethylene-ethylene-propylene-sytrene (SEEPS) and styrene-ethylene propylene (SEP). Such polymers are available for example from Kraton Polymers, Polimeri Europa, Total Petrochemicals, Dexco, and Kuraray. Multiblock or tapered block copolymers (the A-(B-A)$_n$-B type) are available from Firestone. Also, the auxiliary polymer fraction of the hot melt adhesive can contain other polymers like copolymers of ethene, propene or other olefinic monomer, or like copolymerization of acrylic monomers. These additional polymers can be homopolymers, or copolymers and can be potentially modified by any during- or after-polymerization modification like grafting or chain-scission. Blends of various auxiliary polymers may also be employed so long as the composition retains the desired viscosity, creep resistance and low temperature application characteristics of the present invention.

Hot melt adhesive formulas according to the present invention also contain about 0% to about 60%, preferably about 2% to about 30%, and more preferably about 3% to about 20%, by weight, of any plasticizer. A suitable plasticizer may be selected from the group which not only includes the usual plasticizing oils, such as mineral oil, but also olefin oligomers and low molecular weight polymers, glycol benzoates, as well as vegetable and animal oil and derivatives of such oils. The petroleum-derived oils that may be employed are relatively high boiling temperature materials containing only a minor proportion of aromatic hydrocarbons. In this regard, the aromatic hydrocarbons should preferably be less than 30%, and more particularly less than 15%, by weight, of the oil. Alternately, the oil may be totally non-aromatic. The oligomers may be polypropylenes, polybutenes, hydrogenated polyisoprene, hydrogenated butadiene, or the like having average molecular weights between about 100 and about 10,000 g/mol. Suitable vegetable and animal oils include glycerol esters of the usual fatty acids and polymerization products thereof. Other plasticizers may be used provided they have suitable compatibility. Nyflex 222B, a naphthenic mineral oil manufactured by Nynas Corporation, has also been found to be an appropriate plasticizer. As will be appreciated, plasticizers have typically been employed to lower the viscosity of the overall adhesive composition without substantially decreasing the adhesive strength and/or the service temperature of the adhesive. The choice of plasticizer can be useful in formulation for specific end uses (such as wet strength core applications). Because of economics involved in production and in material cost, as plasticizers are usually of lower cost than other materials involved in the formulation like polymers and tackifying resins, the amount of plasticizer in the adhesive should be maximized for cost considerations.

Waxes in amounts of 0% to 20% by weight can also be used in the adhesive composition, and are used to reduce the melt viscosity of the hot melt construction adhesives without appreciably decreasing their adhesive bonding characteristics. These waxes also are used to reduce the open time of the composition without affecting the temperature performance.

The wax material component of the adhesive is optional but when included may comprise up to about 20% by weight of the adhesive composition.

Among the useful wax materials are:

(1) Low molecular weight, that is, 100-6000 g/mol, polyethylene having a hardness value, as determined by ASTM method D-1321, of from about 0.1 to 120 and ASTM softening points of from about 66° C.° to 120° C.;

(2) Petroleum waxes such as paraffin wax having a melting point of from about 130° to 170° F. and microcrystalline wax having a melting point of from about 135° to 200° F., the latter melting points being determined by ASTM method D127-60;

(3) atactic polypropylene having a Ring and Ball softening point of from about 120° to 160° C.;

(4) metallocene catalyzed propylene-based wax like those commercialized by Clariant under the name "Licocene".

(5) metallocene catalyzed wax or single-site catalyzed wax like for example those described in U.S. Pat. Nos. 4,914,253, 6,319,979 or WO 97/33921 or WO 98/03603.

(6) synthetic waxes made by polymerizing carbon monoxide and hydrogen such as Fischer-Tropsch wax; and (7) polyolefin waxes. As used herein, the term "polyolefin wax" refers to those polymeric or long-chain entities comprised of olefinic monomer units. These materials are commercially available from Westlake Chemical Co. under the trade name "Epolene." The materials which are preferred to use in the compositions of the present invention have a Ring and Ball softening point of 200° F. to 350° F. As should be understood, each of these waxes is solid at room temperature. Other useful substances include hydrogenated animal, fish and vegetable fats and oils such as hydrogenated tallow, lard, soy oil, cottonseed oil, castor oil, menhadin oil, cod liver oil, etc., and which are solid at ambient temperature by virtue of their being hydrogenated, have also been found to be useful with respect to functioning as a wax material equivalent. These hydrogenated materials are often referred to in the adhesives industry as "animal or vegetable waxes".

The adhesive also typically includes about 0.1% to about 5% of a stabilizer or antioxidant. The stabilizers which are useful in the hot melt adhesive compositions of the present invention are incorporated to help protect the polymers noted above, and thereby the total adhesive system, from the effects of thermal and oxidative degradation which normally occurs during the manufacture and application of the adhesive as well as in the ordinary exposure of the final product to the ambient environment. Such degradation is usually manifested by a deterioration in the appearance, physical properties and performance characteristics of the adhesive. A particularly preferred antioxidant is Irganox 1010, a tetrakis (methylene(3,5-di-teri-butyl-4-hydroxyhydrocinnamate)) methane manufactured by Ciba-Geigy. Among the applicable stabilizers are high molecular weight hindered phenols and multifunctional phenols, such as sulfur and phosphorus-containing phenols. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency and correspondingly, its reactivity; this steric hindrance thus providing the phenolic compound with its stabilizing properties. Representative hindered phenols include:

1,3,5-trimethyl-2,4,6-tris(3-5-di-tert-butyl-4-hydroxybenzyl) benzene;

pentaerythritol tetrakis-3(3,5-di-tert-butyl-4-hydroxyphenyl) propionate;

n-octadecyl-3(3,5-ditert-butyl-4-hydroxyphenyl) propionate;

4,4'-methylenebis(4-methyl-6-tert butylphenol);

4,4'-thiobis(6-tert-butyl-o-cresol);

2,6-di-tert-butylphenol;

6-(4-hydroxyphenoxy)-2,4-bis(n-ocytlthio)-1,3,5-triazine;

2,4,6-tris(4-hydroxy-3,5-di-tert-butyl-phenoxy)-1,3,5-triazine;

di-n-octadecyl-3,5-di-tert-butyl-4-hydroxybenzylphosphonate;

2-(n-octylthio)ethyl-3,5-di-tert-butyl-4-hydroxybenzoate; and sorbitol hexa-(3,3,5-di-tert-butyl-4-hydroxy-phenyl) propionate.

The performance of these stabilizers may be further enhanced by utilizing, in conjunction therewith; (1) synergists such as, for example, as thiodipropionate esters and phosphites; and (2) chelating agents and metal deactivators as, for example, ethylenediaminetetraacetic acid, salts thereof, and disalicylalpropylenediimine.

The adhesive composition useful in the method of the present invention may be produced using any of the techniques known in the art. A representative example of the procedure involves placing all of the substances, in a jacketed mixing kettle, and preferably in a jacketed heavy duty mixer of the Baker-Perkins or Day type, and which is equipped with rotors, and thereafter raising the temperature of this mixture to a range of 120° C. to 177° C. It should be understood that the precise temperature to be used in this step would depend on the melting point of the particular ingredients. The resulting adhesive composition is agitated until the polymers completely dissolve. A vacuum is then applied to remove any entrapped air.

Up to 25% of optional additives may be incorporated into the adhesive composition in order to modify particular physical properties. These additives may include colorants, such as titanium dioxide and fillers such as talc, calcium carbonate and clay, crosslinking agents, nucleating agents, reactive compounds, fire-retardant mineral or organic agents, as well as ultraviolet light (UV) absorbing agents and UV fluorescing agents. These optional additives are well known in this art.

In certain embodiments, the adhesive formula may contain a fully aromatic or a substantially fully aromatic reinforcing resin. The aromatic or substantially fully aromatic resin should have softening point equal to or higher than 115° C. Examples of such reinforcing resins can be prepared from any substantially aromatic monomers having a polymerizable unsaturated group. Typical examples of such aromatic monomers include the styrenic monomers, styrene, alphamethyl styrene, vinyl toluene, methoxy styrene, tertiary butyl styrene, chlorostyrene, etc., coumarone, indene monomers including indene, and methyl indene. The Ring and Ball Softening Points of the aromatic endblock resin is preferably between 115° and 160° C. More preferably, the softening point is between about 115° and 140° C. and most preferably between about 120° C. and 140° C. Two preferred examples are Plastolyn 240 and Plastolyn 290 available from Eastman chemical. They have Ring and Ball Softening Points of 120° C. and 140° C., respectively. Preferably, styrene and/or alpha-methyl-styrene and/or vinyl-toluene monomers used. They can also be substantially fully hydrogenated aromatic hydrocarbon resins such as Plastolyn R1140 which has a Ring and Ball Softening Point of 140° C. The reinforcing resin should be present in amounts of about 0% to about 20% in the adhesive composition and if present, preferably between about 2% to about 15%, more preferably about 4% to about 12%, and most preferably about 6% to about 10%.

Various methods are conventionally used to coat a hot melt adhesive at fairly low viscosity on a substrate. This can be made by roll coating or any printing type method, or by slot coating, by extrusion or by spray gun. Spray gun techniques are numerous and can be done with or without assistance of compressed air that would shape the adhesive spray, and consequently the adhesive pattern. The hot melt adhesive material is generally allowed to melt in tanks, and then pumped through hoses to the final coating spot on the substrates.

For the present invention, preferred methods of applying the adhesive would be by spray application, most preferably assisted by heated air. Among these techniques, the most common are spiral spray (Controlled Fiberization™ by Nordson), Summit™ by Nordson, Surewrap™ by Nordson, Omega™ by ITW, Curtain Coating™ by Nordson and melt blown process. For the present invention, the temperature at which the hot melt adhesive is applied should be below 170° C., so that the heat sensitive substrates will not be damaged. Preferably, this temperature should be equal to or lower than 160° C., most preferably lower than 150° C.

The viscosity (as measured via ASTM D3236-88) of the adhesive material needs to be generally equal to or lower than 20,000 mPa·s, more preferably lower than 15,000 mPa·s, most preferably lower than 12,000 mPa·s at 163° C. (325° F.) in order to achieve the desired spray pattern and consequently the desired bonding performances (Note: 1 mPa·s equals 1 centipoise). Line speed, add-on levels as well as open time, set time, compression forces and compression time are also process control parameters.

Taking the example of bonding elastic strands in the environment of a diaper manufacturing process, typical conditions are very stringent regarding the adhesive features. The adhesive is typically sprayed either on a polymeric film (usually ethylene based or propylene based under 40 gsm of basis weight), or on elastic strands stretched at up to about 500% from their initial relaxed state, and preferably at about 300% elongation. Film and elastic strands are put in contact together, before, during or after the adhesive spray. The film together with the stretched elastic strands are then laminated to a non-woven web of low basis weight (under 50 gsm). In fact, the primary substrate can also be a non-woven web, and can be the same as the secondary web substrate, when this web is simply sprayed with adhesive and then folded over the elastic strands. Plastic films can have various features like breathability, color, printing, stretchiness, embossing, or surface treatments, for example to favor adhesion from adhesives or inks. Elastic strands can be made of natural or synthetic rubber, of specialty polyurethane formulations, and can be in a strip form, or in a multifilament form. More specifically elastic strands for diaper construction are usually made of polyester polyurethane microfilaments bonded together to get the right elastomeric strength, like Lycra™ or Lycra XA™ from Invista, or narrow bands made of natural or synthetic rubber narrow bands like Fulflex™, from Fulflex Elastomerics.

Line speeds can be as high as 700 feet per minute or higher, and open times are typically less than about 0.5 seconds. Set time is considered as immediate or negligible, as compression into nip rolls is usually helping the adhesive material to set. Add-on levels vary according to the application and the required level of bond strength. The viscosity of the adhesives of the present invention is equal to or lower than 20,000 mPa·s at 163° C. (325° F.). Preferably, it should be lower than 15,000 mPa·s, more preferably below 12,000 mPa·s, as determined by employing a Brookfield Thermocel or other appropriate viscometer and utilizing the testing techniques which are set forth in ASTM Method D3236-88.

The present invention thus encompasses any process of conventional elastic attachment technology as known in the state of the art. The present invention also encompasses any application where various materials can be involved like non-woven materials, polymeric films, and in general elastomeric components put in items like diapers, in a form of strands, films, nonwovens or any other continuous or discrete form. Any substrate material and any substrate form could be used in any combination possible, the adhesive allowing to bond two or more substrates together. Form of substrates can be for example fiber, film, thread, strip, ribbon, coating, foil, sheet, and band. Material of substrate can be a polyolefin, a polyacrylic, a polyester, a polyvinyl chloride, a polystyrene, or a cellulosic like wood, cardboard and paper. The substrate's mechanical behavior can be rigid, plastic or elastomeric. Among elastomeric materials are various examples like natural or synthetic rubber, polyurethane based copolymers, polyether or polyester urethanes, block copolymers of styrene or of amides, or olefinic copolymers. The above list is not limitative, but is only meant to describe examples of what the present invention may encompass.

The present invention encompasses any application where laminates, composites and disposable products are made with the help of bonding parts together with a hot melt adhesive used at a temperature lower than 170° C., preferably equal to or lower than 160° C. while obtaining good cohesion from the adhesive bond to withstand mechanical stress at low, ambient or elevated temperature, in particular under creep conditions. Diapers, adult incontinence products, sanitary napkins and other absorbent disposable products can be envisioned applications for the invention, as well as bed pads, absorbing pads, surgical drapes and other related medical or surgical devices. Construction applications, structural applications or packaging applications, in particular disposable items packaging and food packaging can be applications where the invention is useful. Specifically for elastic attachment, the present invention allows bonding of the elastic strands on film substrates while applying the adhesive at a temperature lower than 170° C., preferably equal to or lower than 160° C. Bonding strength is measured primarily by testing the bond under a specific creep configuration, giving a model of the constraints encountered in a real life cycle of a disposable diaper, where baby movements are stretching the laminates at room temperature or body temperature. Creep test methods can vary among the industry, and the Applicant has developed over the years its own test method that satisfies the majority of the applications seen in the field, and, more important, that can compare and differentiate adhesives from each other, determining if one adhesive is suitable or not for an efficient elastic attachment function, once this adhesive has been coated to form a laminated structure. The creep test can be performed within the first days following the coating operation, and can be performed after a few days or few weeks at elevated temperature, to simulate the effects of ageing under storage and shipping conditions.

Good performance for elastic attachment in a diaper application is typically obtained when the initial bond retention is either more than 60%, preferably more than 70%, more preferably more than 75%, and most preferably more than 80% when the creep test is performed within 2 days after adhesive has been applied on substrates (initial creep test). These conditions are indicative of the level of adhesion and bond retention under creep conditions that can be achieved. These conditions depend on the adhesive application technique used, like spiral spray or Surewrap® for example; on the level of adhesive add-on; on process parameters like air pressure, line speed, and adhesive temperature. Because of economics involved in production and in material cost, preferred adhesive add-ons for a spiral spray application are lower than 18 gsm, more preferably equal to or lower than 15 gsm, most preferably equal to or lower than 12 gsm. If individual strand coating techniques are used, the add-on level is less than 60 mg/strand/meter. For construction applications, the add-on level is typically 6 grams/square meter or less. For other applications, the add-on levels will vary depending on the specific end use requirements.

EXAMPLES

Hot melt adhesive were prepared with the ingredients and mixing procedures described herein below. A total of 2000 grams each were made and the mixing was carried out at about 150° C. to 190° C. under carbon dioxide atmosphere in a laboratory type mixer that consists of a propeller powered by a motor, a heating mantle, a temperature control unit and a container of about 1 gallon in size. The appropriate amounts of each component, calculated according to the ratios shown in the tables below, were added to the container in an appropriate sequence to allow mixing while limiting the heat or shear degradation of ingredients. After the ingredients in the container were completely melted and mixed thoroughly to allow a good visual homogeneity, samples were stored appropriately to be tested.

Laminated specimens were formed by using a high speed laboratory coater, at 800 feet per minute. When a spiral spray technique was used, the coater was fitted with a conventional 0.018-inch to 0.020-inch diameter spiral spray extrusion nozzle, with 12 air holes, available from Nordson Corporation. When Surewrap® technique was used, the coater was fitted with a 3-strands 0.018 inch diameter extrusion nozzle available from Nordson Corporation. Adhesives were sprayed at various coating weights, depending on the application required, with different open times—typically 0.05 to 0.1 seconds—to the 1-bar-nip rolls compression.

Standard polypropylene-based spun-bond non-woven web is available from BBA Corporation at 15.7 gram per square meter coating weight. Standard polyethylene non-breathable treated and embossed white film at 17 gram per square meter is available under trade name DH-216 from Clopay Corporation. Standard spandex strands are available from Invista, under the Trademark Lycra XA, and the grade used is 262P, at 800 decitex.

When spiral spray is used, the spray head is generally perpendicular to the substrate and at a height between 0.5 and 1 inch to get a 12 to 14 mm wide pattern into the laminated structure, covering 3 parallel strands of Lycra material with 5 mm in-between them.

Creep Resistance or bond retention test is carried out with the laminated specimens containing elastic strands. The specimen, cut to about 350 mm in length, is stretched out completely and its ends were securely attached to a piece of rigid board. A length of 300 mm was marked in the machine direction and the elastic strands are cut at the marks. The specimen is then placed in an air-circulating oven at 38° C. Under these conditions, the stretched elastic strands can retract or contract to a certain distance. The distance between the ends of each elastic strand is measured after four hours. The ratio of the final length to the initial length, defined as bond Retention and expressed in percentage (%), is a measure of the ability of the adhesive to hold the elastic strands. This ratio is measured on 8 to 12 elastic strands and the result is then averaged. If this test is performed within 2 days after the adhesive coating has been done, it is called the initial creep test. If it is performed after the specimen have been put in an oven at 38° C. or higher one week after the coating operation, this test is called the one-week-aged creep test.

The procedure for performing the Creep Test is as follows:

Background: The elastic at a certain elongation (250% or 300% stretched) is sandwiched in between two (2) substrates (primary and secondary substrates) using an adhesive to form a laminate.

Purpose: This test is to measure the movement of elastic or "creep," from the primary and secondary substrates.

Procedure:

A. Using the stapler, secure one end of the laminate into the corrugated board. Stretch out the laminate to the full extension, making sure not to overstretch the lamination. Then, secure the other end of the laminate.

B. Using the ruler, mark across the elastic a length of approximately 300 mm.

C. Once all of the samples are secured and marked, cut with a razor across each of the strands of elastic.

D. Place the test samples into the oven, usually set at 38° C., and test. The samples should be checked after 4 hours. Mark the ends of each elastic strand and measure the % Creep Retention or % Creep.

E. Laminate samples are aged at elevated temperature (>38° C.) for 1 Week (or longer) to determine the % Creep Retention over time. Laminates are conditioned overnight at room temperature prior to testing.

Example Calculations:

$$\text{Initial Laminate} = 300 \text{ mm}$$

$$\text{Laminate after 4 hours} = 250 \text{ mm}$$

$$\% \text{ Creep Retention} = \frac{\text{Length of lamination after } \times \text{ hours}}{\text{Length of initial lamination}} \times 100\%$$

$$\% \text{ Creep Retention} = \frac{250 \text{ mm}}{300 \text{ mm}} \times 100\%$$

$$\% \text{ Creep Retention} = 83.0\%$$

Storage modulus (G'), Tg and Txover were determined using a TA Instruments Ares rheometer. The parallel plates used had a diameter of 25 millimeters and a 1.6 millimeter gap. The instrument was set to a frequency of 10 rads/sec and the temperature sweep was performed from 140° C. to −40° C.

Peel strengths were determined at 180° on an Instron tensile testing machine at a crosshead speed of 12 inches/minute at room temperature (i.e. about 72° F.).

The raw materials used in the various compositions shown in examples and described in the present specification are defined as follows:

| Raw Material Name | Type | Supplier | Physical Properties & Test Methods | | | |
|---|---|---|---|---|---|---|
| | Mineral Oils | | Viscosity @ 40° C. | | | |
| Nynas 222B | Hydrotreated Naphthenic Process Oil | Nynas | 90-110 cP | ASTM D445 | | |
| Kaydol | White Mineral Oils | Sonneborn, Inc. | 64.5-69.7 cP | ASTM D445 | | |
| | | | Viscosity (SUS) @ 100° C. | | Specific Gravity @ 15.5° C. | |
| Indopol H100 | Polybutene | Ineos | 1025 cP | ASTM D1218 | 0.893 | D1298 |
| | Tackifying Resins | Supplier | Ring & Ball Softening Point | | | |
| Eastotac H100R | Partially Hydrogenated Aliphatic Hydrocarbon resin | Eastman | 100° C. | ASTM E28 | | |
| Piccotac 9095 | Aromatic modified C5 Hydrocarbon resin | Eastman | 95° C. | ASTM E28 | | |
| Eastotac H115L | Hydrogenated Aliphatic Hydrocarbon resin | Eastman | 115° C. | ASTM E28 | | |
| Escorez 5400 | Hydrogenated DCPD | ExxonMobil | 100° C. | ASTM E28 | | |
| Escorez 5340 | Hydrogenated DCPD | ExxonMobil | 140° C. | ASTM E28 | | |

-continued

| | | | | | |
|---|---|---|---|---|---|
| Sukorez SU210 | Fully Hydrogenated Aliphatic Hydrocarbon resin | Kolon Chemical Co. Ltd. | 110° C. | ASTM E28 | |
| Plastolyn 290 | Pure Monomer Resin - Alpha Methyl Styrene | Eastman | 140° C. | ASTM E28 | |

| | Primary Polymer | Supplier | Density | | Melt Index | | Melt Enthalpy (J/g) Bostik Data |
|---|---|---|---|---|---|---|---|
| Infuse 9817 | OBC (Olefin Block Copolymer) | Dow | 0.877 g/cm³ | ASTM D792 | 15.0 g/10 min (190° C./2.16 Kg) | ASTM D1238 | 42.6 |
| Infuse 9807 | OBC (Olefin Block Copolymer) | Dow | 0.866 g/cm³ | ASTM D792 | 15.0 g/10 min (190° C./2.16 Kg) | ASTM D1238 | 23.0 |
| Infuse 9507 | OBC (Olefin Block Copolymer) | Dow | 0.866 g/cm³ | ASTM D792 | 5.0 g/10 min (190° C./2.16 Kg) | ASTM D1238 | |

| | Secondary Polymer | Supplier | Density | | Melt Index | | Melt Enthalpy (J/g) Bostik Data |
|---|---|---|---|---|---|---|---|
| Affinity GA 1900 | Ethylene-Octene Copolymer | Dow | 0.870 g/cm³ | ASTM D792 | 1,000 g/10 min (190° C./2.16 Kg) | ASTM D1238 | 69.3 |
| Vistamaxx 6202 | Propylene-Ethylene Copolymer (15% C₂) | ExxonMobil | 0.861 g/cm³ | ASTM D1505 | 18 g/10 min (230° C./2.16 kg.) | ASTM D1239 | 15.3 |
| Vistamaxx 2320 | Propylene-Ethylene Copolymer (14% C₂) | ExxonMobil | 0.864 g/cm³ | ASTM D1505 | 200 g/10 min (230° C./2.16 kg.) | | 10.4 |
| Licocene P1302 | Metallocene Polypropylene Wax | Clariant | 0.870 g/cm³ | ISO 1183 | | | 39.0 |
| Epolene C-10 | Highly branched Polyethylene | Eastman | 102° C. | ASTM E28 | | | 91.3 |
| Bareco PX105 | Fischer Tropsch (FT), Synthetic Wax | Baker Petrolite Polymers | 105° C. | ASTM E28 | | | 225.6 |
| Escorene MV 2514 | Ethylene Vinyl Acetate (14% VA) | ExxonMobil | 0.925 g/cm³ | | | | 77.6 |
| EOD-02-15 | Metallocene Polypropylene Copolymer | Total Petrochemical | | | 12.0 g/10 min (230° C./2.16 Kg) | ASTM D1238 | 75.7 |

| | | Supplier | Brookfield, Viscosity @ 190° C. | | Ring & Ball Softening Point | | Melt Enthalpy (J/g) Bostik Data |
|---|---|---|---|---|---|---|---|
| Eastoflex E1060 | Amorphous Polyolefin (APO's), -Propylene based polymer | Eastman | 6000 cP | ASTM D3236 | 135° C. | ASTM E28 | 11.6 |
| Eastoflex E1200 | Amorphous Polyolefin (APO's), -Propylene based polymer | Eastman | 20000 cP | ASTM D3236 | 135° C. | ASTM E28 | 16.3 |
| Vestoplast 704 | Amorphous polyalpha-olefin (Propene-rich) polymer | Evonik Degussa Corporation | 3500 cP | ASTM D3236 | 105° C. | ASTM E28 | 17.6 |

| | | Supplier | % Styrene |
|---|---|---|---|
| Septon 4033 | Hydrogenated poly(styrene-b-isoprene/b-butadiene-b-styrene) | Septon Co, of America | 30.0% Styrene |

| | Antioxidant | Supplier | Flash Point (° C.) | Melting Range (° C.) |
|---|---|---|---|---|
| Irganox 1010 | Hindered Phenol. | Ciba Specialty | 297 | 110-125 |

"APAO" as used herein is an abbreviation for "amorphous polyalphaolefin."
"HC" as used herein is an abbreviation for "hydrocarbon."
"OBC" as used herein is an abbreviation for "olefin block copolymer."
"SB" as used herein is an abbreviation for "styrene-butadiene."
"SI" as used herein is an abbreviation for "styrene-isoprene."
"SIBS" as used herein is an abbreviation for "styrene-isoprene-butadiene-styrene."
"SEBS" as used herein is an abbreviation for "styrene-ethylene-butadiene-styrene."
"SEB" as used herein is an abbreviation for "styrene-ethylene-butylene."
"SEP" as used herein is an abbreviation for "styrene-ethylene-propylene."
"SEEPS" as used herein is an abbreviation for "styrene-ethylene-ethylene-propylene-styrene."
"EVA" as used herein is an abbreviation for "ethylene-vinyl-acetate."
"SIS" as used herein is an abbreviation for "styrene-isoprene-styrene."
"SBS" as used herein is an abbreviation for "styrene-butadiene-styrene."
"SEPS" as used herein is an abbreviation for "styrene-ethylene-propylene-styrene."
"SBBS" as used herein is an abbreviation for "styrene-butadiene-butadiene-styrene."
"SPP" as used herein is an abbreviation for "syndiotactic polypropylene."

The invention is further illustrated by way of the specific examples that are set forth below.

Example 1

Table 1 illustrates four different compositions prepared according to the present invention using the lower density grade of OBC (Infuse™ 9807) and compares them to a composition containing no secondary polymer (45-B) as well as to a commercially available SBS-based hot melt adhesive (H4237) available from Bostik Inc. for elastic attachment applications. Table 1 illustrates the initial creep resistance results of the compositions described when the adhesive add-on is 12 grams/meter$^2$ (gsm), in spiral spray configuration. Table 1 demonstrates that formula 45-B has inadequate creep resistance, while formulae 50-G, 50-H, 50-I and 50-K all have adequate creep resistance and which are comparable to H4237. From these results, it is clear that the formulas 50-G, 50-H, 50-I and 50-K are suitable to fulfill the requirements the present invention has described.

Example 2

Table 2 illustrates six different compositions prepared according to the present invention using the higher density grade of OBC (Infuse™ 9817) and compares them to a commercially available SBS-based hot melt adhesive (H4237) available from Bostik Inc. for elastic attachment applications. Table 2 also illustrates the initial creep test results of the compositions described in Table 2 when the adhesive add-on is 12 gsm, in spiral spray configuration. Table 2 demonstrates that formulae AI, AJ, AK, AM, 50-N and 50-O all have adequate creep resistance and which are comparable to H4237. From these results, it is clear that the formulas AI, AJ, AK, AM, 50-N and 50-O are suitable to fulfill the requirements the present invention has described.

TABLE 1

| Raw Material | 1712-45B | 1712-50-G | 1712-50-H | 1712-50-I | 1712-50-K | H4237 |
|---|---|---|---|---|---|---|
| Nynas 222B | 16 | 10 | 14 | 14 | 10 | |
| Eastoflex 1060 | | 6 | 6 | | | |
| Eastoflex 1200 | | 8.5 | | 11 | 9.5 | |
| Eastotac H100R | 63.5 | 60 | 59.5 | 59.5 | 60 | |
| Infuse 9807 | 20 | 10 | 15 | 10 | 15 | |
| EOD-02-15 | | 5 | | | | |
| Septon 4033 | | | 5 | 5 | | |
| Epolene C-10 | | | | | 5 | |
| Irganox 1010 | 0.5 | 0.5 | 0.5 | 0.5 | 0.5 | |
| Total | 100 | 100 | 100 | 100 | 100 | |
| Physical Properties | | | | | | |
| Viscosity at 163° C., cP | 7162 | 12050 | 9375 | 6550 | 6950 | 7900 |
| Softening Pt (Herzog, Glycerin, ° C.) | 106 | 114 | 109 | 109 | 108 | 92 |
| Tg, ° C. | 32 | 27.7 | 23.5 | 25.4 | 33 | |
| Txover, ° C. | 69 | 63 | 69.3 | 63.2 | 67.4 | |
| G' @ 25° C. (dynes/cm$^2$) | $1.04 \times 10^7$ | $4.03 \times 10^6$ | $3.28 \times 10^6$ | $2.65 \times 10^6$ | $1.49 \times 10^7$ | |
| Percent (%) Creep Retention at 38° C. | | | | | | |
| Initial | 45 | 63 | 67 | 69 | 72 | 70 |

TABLE 2

| Raw Material | 1712-AI | 1712-AJ | 1712-AK | 1712-AM | 1712-50-N | 1712-50-O | H4237 |
|---|---|---|---|---|---|---|---|
| Nynas 222B | 10 | 10 | 10 | 10 | 10 | 14 | |
| Eastoflex 1060 | 14.5 | 14.5 | 12.5 | 12.5 | 14.5 | | |
| Eastoflex 1200 | | | | | | 11 | |
| Escorez 5400 | 30 | | 60 | 30 | | | |
| Escorez 5340 | 30 | 30 | | 30 | | | |
| Piccotac 9095 | | 30 | | | | | |
| Eastotac H100R | | | | | 60 | 59.5 | |
| Infuse 9817 | 15 | 15 | 17 | 15 | 15 | 15 | |
| Bareco PX105 | | | | 2 | | | |
| Irganox 1010 | 0.5 | 0.5 | 0.5 | 0.5 | 0.5 | 0.5 | |
| Total | 100 | 100 | 100 | 100 | 100 | 100 | |
| Physical Properties | | | | | | | |
| Viscosity at 163° C., cP | 7525 | 8525 | 8300 | 6925 | 7850 | 6975 | 7900 |
| Softening Pt (Herzog, Glycerin, ° C.) | 114 | 112 | 113 | 113 | 113 | 114 | 92 |
| Tg, ° C. | 40.2 | 40.3 | 32 | Not Available | 35.6 | 32 | |
| Txover, ° C. | 76.3 | 75.9 | 78.7 | Not Available | 79.1 | 79.1 | |
| G' @ 25° C. (dynes/cm$^2$) | $3.61 \times 10^7$ | $3.45 \times 10^7$ | $1.44 \times 10^7$ | Not Available | $2.43 \times 10^7$ | $1.71 \times 10^7$ | |
| Percent (%) Creep Retention at 38° C. | | | | | | | |
| Initial | 62 | 71 | 66 | 62 | 62 | 70 | 70 |

Example 3

Table 3 and 3A illustrate numerous different compositions prepared according to the present invention, (except 50N-26, 50N-27 and 50N-28 which are prior art compositions from WO 2006/102150 and 50N-9 which has no secondary polymer) containing different polymer blends, and compared to a commercially available SBS-based hot melt adhesive (H4237) available from Bostik Inc. for elastic attachment applications. Tables 3 and 3A also illustrate the initial % creep retention for the compositions described in Tables 3 and 3A, when the adhesive add-on is 12 gsm in spiral spray configuration. From these results, it is clear that the formulas (except for the three prior art compositions and 50N-9 noted above) are suitable to fulfill the requirements the present invention has described. In addition, examples 50N-9, 50N-11 and 50N-12 illustrate that as the amount of secondary polymer increases from 0% to 11% to 20%, respectively, the creep retention also increases.

TABLE 3

| Raw Material | 1712-50N | 1712-50N-3 | 1712-50N-9 | 1712-50N-11 | 1712-50N-12 | 1712-50N-13 |
|---|---|---|---|---|---|---|
| Nynas 222B | 10 | | 24.5 | 14 | 5 | 10 |
| Kaydol | | 10 | | | | |
| Eastoflex 1060 | 14.5 | 14.5 | | 11 | 20 | 14.5 |
| Eastotac H100R | 60 | 60 | 60 | 59.5 | 59.5 | 55 |
| Eastotac H115L | | | | | | |
| Infuse 9817 | 15 | 15 | 15 | 15 | 15 | 15 |
| Infuse 9507 | | | | | | |
| Vestoplast 704 | | | | | | |
| Plastolyn 290 | | | | | | 5 |
| Irganox 1010 | 0.5 | 0.5 | 0.5 | 0.5 | 0.5 | 0.5 |
| Total | 100 | 100 | 100 | 100 | 100 | 100 |
| Physical Properties | | | | | | |
| Viscosity at 163° C., cP | 7850 | 6150 | 1945 | 4775 | 9550 | 7550 |
| Softening Pt (Herzog, Glycerin, ° C.) | 112 | 114 | 107 | 112 | 117 | 115 |
| Tg, ° C. | 35.9 | 36.7 | 30.9 | 35 | 37.9 | 39.3 |
| Txover, ° C. | 75 | 78.4 | 72.1 | 77.6 | 77.6 | 79.6 |
| G' @ 25° C. (dynes/cm$^2$) | $1.63 \times 10^7$ | $2.23 \times 10^7$ | $6.70 \times 10^6$ | $1.75 \times 10^7$ | $2.46 \times 10^7$ | $2.62 \times 10^7$ |
| Percent (%) Creep Retention at 38° C. | | | | | | |
| Initial | 62 | 67 | 36 | 64 | 79 | 82 |

| Raw Material | 1712-50N-19 | 1712-50N-25 | 1712-50N-26 | 1712-50N-27 | 1712-50N-28 | H4237 |
|---|---|---|---|---|---|---|
| Nynas 222B | 10 | 10 | | | | |
| Kaydol | | | 25 | 25 | 25 | |
| Eastoflex 1060 | | 14.5 | | | | |
| Eastotac H100R | 60 | | | 55 | 55 | 55 |
| Eastotac H115L | | 60 | | | | |
| Infuse 9817 | 15 | 15 | | | | 20 |

TABLE 3-continued

|  |  |  |  |  |  |  |
|---|---|---|---|---|---|---|
| Infuse 9507 |  |  | 20 |  |  |  |
| Vestoplast 704 | 14.5 |  |  |  |  |  |
| Plastolyn 290 |  |  |  |  |  |  |
| Irganox 1010 | 0.5 | 0.5 | 0.5 | 0.5 | 0.5 |  |
| Total | 100 | 100 | 100.5 | 100.5 | 100.5 |  |
| Physical Properties | | | | | | |
| Viscosity at 163° C., cP | 6112 | 7637 | 11650 | 4512 | 3975 | 7900 |
| Softening Pt (Herzog, Glycerin, ° C.) | 112 | 114 | 109 | 102 | 110 | 92 |
| Tg, ° C. | 38 | ~43.0 | 10.7 | 11.8 | 20.3 |  |
| Txover, ° C. | 80.7 | 77.3 | 77 | 65.6 | 79.6 |  |
| G' @ 25° C. (dynes/cm$^2$) | $1.90 \times 10^7$ | $<3.0 \times 10^7$ | $1.75 \times 10^6$ | $1.41 \times 10^6$ | $4.52 \times 10^6$ |  |
| Percent (%) Creep Retention at 38° C. | | | | | | |
| Initial | 78 | 64 | 34 | 31 | 32 | 70 |
|  |  |  | Example 84 of Dow's WO 2006/102150 A2 | Example 84 of Dow's WO 2006/102150 A2 | Example 84 of Dow's WO 2006/102150 A2 |  |

TABLE 3A

| Raw Material | 1712-50N-37 | 1712-50N-38 | 1712-50N-40 | 1712-50N-41 | 1712-50N-42 | 1712-50N-43 |
|---|---|---|---|---|---|---|
| Nynas 222B | 10 | 10 | 10 | 10 | 10 |  |
| Indopol H-100 |  |  |  |  |  |  |
| Eastoflex 1060 |  |  |  |  | 19.5 |  |
| Eastotac H100R | 60 | 60 | 60 | 60 | 60 | 60 |
| Epolene C10 | 14.5 |  |  |  |  |  |
| Escorene MV 2514 |  | 14.5 |  |  |  |  |
| Affinity GA 1900 |  |  | 14.5 |  |  | 24.5 |
| Vistamaxx 6202 |  |  |  | 14.5 |  |  |
| Vistamaxx 2320 |  |  |  |  |  |  |
| Licocene PP1302 |  |  |  |  |  |  |
| Infuse 9817 | 15 | 15 | 15 | 15 | 10 | 15 |
| Irganox 1010 | 0.5 | 0.5 | 0.5 | 0.5 | 0.5 | 0.5 |
| Total | 100 | 100 | 100 | 100 | 100 | 100 |
| Physical Properties | | | | | | |
| Viscosity at 163° C., cP | 5200 | 4700 | 6365 | 40500 | 3480 | 12520 |
| Softening Pt (Herzog, Glycerin, ° C.) | 109 | 110 | 111 | 114 | 109 | 102 |
| Percent (%) Creep Retention at 38° C. | | | | | | |
| Initial | 76 | 72 | 74 | 75 | 60 | 81 |

| Raw Material | 1712-50N-44 | 1712-50N-45 | 1712-50N-47 | 1712-50N-48 | H4237 |
|---|---|---|---|---|---|
| Nynas 222B | 10 | 10 |  | 10 |  |
| Indopol H-100 |  |  | 10 |  |  |
| Eastoflex 1060 | 9.5 |  | 14.5 |  |  |
| Eastotac H100R | 60 | 60 | 60 | 60 |  |
| Epolene C10 |  |  |  |  |  |
| Escorene MV 2514 |  |  |  |  |  |
| Affinity GA 1900 |  |  |  |  |  |
| Vistamaxx 6202 |  |  |  |  |  |
| Vistamaxx 2320 |  |  |  | 14.5 |  |
| Licocene PP1302 |  | 14.5 |  |  |  |
| Infuse 9817 | 20 | 15 | 15 | 15 |  |
| Irganox 1010 | 0.5 | 0.5 | 0.5 | 0.5 |  |
| Total | 100 | 100 | 100 | 100 |  |
| Physical Properties | | | | | |
| Viscosity at 163° C., cP | 11250 | 3400 | 8125 | 22620 | 7900 |
| Softening Pt (Herzog, Glycerin, ° C.) | 114 | 111 | 114 | 126 | 92 |
| Percent (%) Creep Retention at 38° C. | | | | | |
| Initial | 81 | 68 | 79 | 76 | 70 |

Example 4

Table 4 shows the initial and the one-week aged peel strengths of five different compositions (42-J-A, 42-J-B, 42-J-C, 110 and 100-A) with an adhesive add-on of 4 gsm when used in a construction application using polyethylene (PE) film and nonwoven (NW) substrates. These five formulae are compared to three different compositions (42, 42-F and 42-J) that contain OBC but no secondary polymer, as well as to a commercially available SBS-based hot melt adhesive (H4073) available from Bostik, Inc. for construction applications. From these results, it is clear that the formulae 42-J-A, 42-J-B, 42-J-C, 110 and 100-A are suitable to fulfill the requirements the present invention has described because they all have adequate peel strengths, which are comparable to H4073, but formulae 42, 42-F and 42-J have higher than desirable viscosity, and are thus not suitable for construction applications.

TABLE 4

| Raw Material | 1742-42 | 1712-42-F | 1712-42-J | 1712-42-J-A | 1712-42-J-B | 1712-42-J-C | 1712-110 | 1712-110-A | H4073 |
|---|---|---|---|---|---|---|---|---|---|
| Nynas 222B | 21 | 21 | 21 | 18 | 18 | 21 | 21 | 21 | |
| Eastoflex 1060 | | | | 8 | 10.5 | 10 | | | |
| Affinity GA 1900 | | | | | | | 10 | 8 | |
| Eastotac H100R | 57.5 | | | | 30 | | | | |
| Piccotac 9095 | | | 57.5 | 57.5 | 30 | 57.5 | 57.5 | 58.5 | |
| Sukorez SU210 | | 57.5 | | | | | | | |
| Infuse 9807 | 21 | 21 | 21 | 16 | 11 | 11 | 11 | 12 | |
| Irganox 1010 | 0.5 | 0.5 | 0.5 | 0.5 | 0.5 | 0.5 | 0.5 | 0.5 | |
| Total | 100 | 100 | 100 | 100 | 100 | 100 | 100 | 100 | |
| Physical Properties | | | | | | | | | |
| Viscosity at 149° C., cP | 11070 | 11020 | 7812 | 5642 | 2920 | 2400 | 2325 | 2470 | 2800 |
| SP, ° C. | 107 | 106 | 107 | 103 | 103 | 102 | 90 | 90 | 78 |
| Tg, ° C. | 23° C. | 20° C. | 20° C. | 21° C. | 23° C. | 21° C. | 20.3° C. | 20.0° C. | 23° C. |
| Txover, ° C. | 69° C. | 69° C. | 69° C. | 45° C. | G" Predominant | G" Predominant | G" Predominant | G" Predominant | 73° C. |
| G' @ 25° C. | $4.58 \times 10^6$ | $3.46 \times 10^6$ | $2.81 \times 10^6$ | $2.54 \times 10^6$ | $1.67 \times 10^6$ | $9.17 \times 10^5$ | $1.25 \times 10^6$ | $1.27 \times 10^6$ | $1.34 \times 10^6$ |
| Average Peel Force (Grams), 4.0 GSM Add-on, 3 Spirals, PE/NW | | | | | | | | | |
| Initial | 689 | 715 | 444 | 270 | 484 | 399 | 400 | 410 | 340 |
| 1 Week Aged @ 54° C. | 928 | 815 | 526 | 402 | 805 | 602 | 600 | 600 | 411 |

The invention claimed is:

1. A hot melt adhesive composition, comprising a blend of the following components: about 5% to about 50% by weight of an olefin block copolymer; about 10% to about 70% by weight of a first tackifying resin having a softening point of at least about 95° C.; about 0 to 65% of second tackifying resin different than the first tackifying resin; about 0 to about 60% by weight of a plasticizer; and about 0% to about 20% by weight of an aromatic reinforcing resin having a softening point equal to or higher than 115° C.; about 1% to about 40% by weight of a secondary polymer having a relatively low crystallinity, which low crystallinity is greater than about 30 Joules/gram and equal to or less than 250 Joules/gram, said secondary polymer selected from the group consisting of a single cite or metallocene catalyzed ethylene-based copolymer having a $C_3$ to $C_{18}$ alpha-olefin comonomer, a single site or metallocene catalyzed propylene-ethylene copolymer, a blend of the ethylene-based copolymers, a blend of the propylene-ethylene copolymers, and a blend of one or more of the ethylene-based copolymers with one or more of the propylene-ethylene copolymers, said secondary polymer being a polymer that is different from the olefin block copolymer, the first and second tackifying resins, and the reinforcing resin; and about 0.1% to about 5% by weight of a stabilizer; wherein the components total 100% by weight of the composition, and the viscosity of the composition is equal to or less than about 20,000 mPa·s at 163° C.

2. The composition of claim 1 further including about 1% to about 25% by weight of an auxiliary polymer selected from the group consisting of SB, SI, SIS, SBS, EVA, SEB, SEEPS, SIBS, SEBS, SEP, SEPS, SBBS and blends thereof, said auxiliary polymer being a polymer that is different from the olefin block copolymer, the first and second tackifying resins, the reinforcing resin, and the secondary polymer.

3. The composition of claim 1 comprising about 10% to about 30% by weight of said olefin block copolymer.

4. The composition of claim 1 comprising about 12% to about 20% by weight of said olefin block copolymer.

5. The composition of claim 1 comprising about 2% to about 30% by weight of said plasticizer.

6. The composition of claim 1 wherein said first tackifying resin has a softening point of from about 95° C. to about 140° C.

7. The composition of claim 1 wherein said composition has a viscosity equal to or less than 15,000 mPa·s at 163° C.

8. The composition of claim 1 wherein said composition has a viscosity equal to or less than 12,000 mPa·s at 163° C.

9. The composition of claim 1 comprising about 2% to about 15% of said aromatic reinforcing resin.

10. The composition of claim 1 wherein the aromatic reinforcing resin is a product from pure monomer polymerization.

11. The composition of claim 1 wherein the aromatic reinforcing resin has a softening point of from about 115° C. to about 160° C.

12. The composition of claim 1 wherein the aromatic reinforcing resin has a softening point of from about 115° C. to about 140° C.

13. The composition of claim 1 wherein the aromatic reinforcing resin has a softening point of from about 120° C. to about 140° C.

14. The composition of claim 1 having about 40% to about 65% by weight of said first tackifying resin.

15. The composition of claim 1 having about 50% to about 60% by weight of said first tackifying resin.

16. The composition of claim 1 wherein said composition has an initial bond retention of at least about 60%.

17. The composition of claim 1 wherein said composition has an initial bond retention of at least about 70%.

18. The composition of claim 1 wherein said composition has an initial bond retention of at least about 80%.

19. The composition of claim 1 wherein said secondary polymer has a crystallinity greater than about 30 Joules/gram and equal to or less than 150 Joules/gram.

20. The composition of claim 1 wherein said secondary polymer has a crystallinity greater than about 30 Joules/gram and equal to or less than 100 Joules/gram.

21. The composition of claim 1 comprising about 2% to about 30% by weight of said secondary polymer.

22. The composition of claim 1 wherein the first tackifying resin is selected from the group consisting of aliphatic hydrocarbon resins and their hydrogenated derivatives, hydrogenated cycloaliphatic hydrocarbon resins, aromatic modified aliphatic or hydrogenated cycloaliphatic hydrocarbon resins, aliphatic modified aromatic hydrocarbon resins, partially or fully hydrogenated aromatic hydrocarbon resins, polyterpene and styrenated polyterpene resins.

23. The composition of claim 1 wherein said plasticizer is selected from the group consisting of mineral oil and liquid polybutene.

24. The composition of claim 1 further including a wax selected from the group consisting of petroleum waxes, microcrystalline waxes, low molecular weight polyethylene and polypropylene, synthetic waxes and polyolefin waxes.

\* \* \* \* \*